(12) United States Patent
Liu et al.

(10) Patent No.: US 9,870,869 B1
(45) Date of Patent: Jan. 16, 2018

(54) WET ELECTROLYTIC CAPACITOR

(71) Applicant: AVX Corporation, Fountain Inn, SC (US)

(72) Inventors: Yanming Liu, Simpsonville, SC (US); Jason Laforge, Naples, ME (US)

(73) Assignee: AVX Corporation, Fountain Inn, SC (US)

( * ) Notice: Subject to any disclaimer, the term of this patent is extended or adjusted under 35 U.S.C. 154(b) by 10 days.

(21) Appl. No.: 15/195,103

(22) Filed: Jun. 28, 2016

(51) Int. Cl.
| | |
|---|---|
| *H01G 9/145* | (2006.01) |
| *A61N 1/39* | (2006.01) |
| *H01G 9/035* | (2006.01) |
| *H01G 9/07* | (2006.01) |
| *H01G 9/052* | (2006.01) |
| *H01G 9/042* | (2006.01) |
| *H01G 9/08* | (2006.01) |
| *H01G 9/10* | (2006.01) |

(52) U.S. Cl.
CPC ............ *H01G 9/145* (2013.01); *A61N 1/3956* (2013.01); *A61N 1/3975* (2013.01); *H01G 9/035* (2013.01); *H01G 9/0425* (2013.01); *H01G 9/0525* (2013.01); *H01G 9/07* (2013.01); *H01G 9/08* (2013.01); *H01G 9/10* (2013.01)

(58) Field of Classification Search
None
See application file for complete search history.

(56) References Cited

U.S. PATENT DOCUMENTS

| | | |
|---|---|---|
| 4,017,302 A | 4/1977 | Bates et al. |
| 4,441,927 A | 4/1984 | Getz et al. |
| 4,483,819 A | 11/1984 | Albrecht et al. |
| 4,555,268 A | 11/1985 | Getz |
| 5,082,491 A | 1/1992 | Rerat |
| 5,232,169 A | 8/1993 | Kaneko et al. |
| 5,369,547 A | 11/1994 | Evans |

(Continued)

FOREIGN PATENT DOCUMENTS

| | | |
|---|---|---|
| EP | 1 737 005 B1 | 3/2010 |
| EP | 1 607 991 B1 | 7/2010 |

(Continued)

OTHER PUBLICATIONS

Related Application Form.
International Search Report and Written Opinion for PCT/US2017/037829 dated Sep. 28, 2017, 11 pages.

*Primary Examiner* — Dion R Ferguson
(74) *Attorney, Agent, or Firm* — Dority & Manning, P.A.

(57) ABSTRACT

A wet electrolytic capacitor that contains a casing that contains a sidewall extending to an upper end to define an opening is provided. The sidewall further defines an inner surface that surrounds an interior. At least one anode and at least one cathode are positioned within the interior of the casing, wherein the cathode contains an electrochemically-active material and further wherein an anode lead extends from the anode. A working electrolyte is in electrical contact with the anode and the electrochemically-active material. The capacitor also comprises a lid assembly that contains a lid positioned on an upper end of the casing sidewall, wherein the lid defines an orifice through which a tube extends. The tube accommodates the anode lead that extends from the anode. A dielectric layer is formed on a surface of the tube.

25 Claims, 4 Drawing Sheets

(56) References Cited

U.S. PATENT DOCUMENTS

| | | | |
|---|---|---|---|
| 5,457,862 A | 10/1995 | Sakata et al. | |
| 5,473,503 A | 12/1995 | Sakata et al. | |
| 5,522,558 A | 6/1996 | Kaneko | |
| 5,726,118 A | 3/1998 | Ivey et al. | |
| 5,729,428 A | 3/1998 | Sakata et al. | |
| 5,776,632 A | 7/1998 | Honegger | |
| 5,786,980 A | 7/1998 | Evans | |
| 5,812,367 A | 9/1998 | Kudoh et al. | |
| 5,858,911 A | 1/1999 | Wellen et al. | |
| 5,926,362 A | 7/1999 | Muffoletto et al. | |
| 5,954,856 A | 9/1999 | Pathare et al. | |
| 6,117,195 A | 9/2000 | Honegger | |
| 6,126,097 A | 10/2000 | Chen et al. | |
| 6,145,765 A | 11/2000 | Capelle, Jr. et al. | |
| 6,197,252 B1 | 3/2001 | Bishop et al. | |
| 6,238,456 B1 | 5/2001 | Wolf et al. | |
| 6,322,912 B1 | 11/2001 | Fife | |
| 6,334,879 B1 | 1/2002 | Muffoletto et al. | |
| 6,361,898 B1 | 3/2002 | Honegger | |
| 6,391,275 B1 | 5/2002 | Fife | |
| 6,416,730 B1 | 7/2002 | Fife | |
| 6,527,937 B2 | 3/2003 | Fife | |
| 6,576,038 B1 | 6/2003 | Rao | |
| 6,576,099 B2 | 6/2003 | Kimmel et al. | |
| 6,576,524 B1 | 6/2003 | Evans et al. | |
| 6,592,740 B2 | 7/2003 | Fife | |
| 6,594,140 B1 | 7/2003 | Evans et al. | |
| 6,613,474 B2 | 9/2003 | Frustaci et al. | |
| 6,639,787 B2 | 10/2003 | Kimmel et al. | |
| 6,707,660 B1 | 3/2004 | Evans et al. | |
| 6,721,170 B1 | 4/2004 | Evans et al. | |
| 6,850,405 B1 | 2/2005 | Mileham et al. | |
| 6,859,353 B2 | 2/2005 | Elliott et al. | |
| 6,946,220 B2 | 9/2005 | Probst et al. | |
| 6,967,829 B2 | 11/2005 | Seitz et al. | |
| 6,986,796 B2 | 1/2006 | Warchocki et al. | |
| 6,987,663 B2 | 1/2006 | Merker et al. | |
| 7,003,024 B2 | 2/2006 | Kubo et al. | |
| 7,012,799 B2 | 3/2006 | Muffoletto et al. | |
| 7,072,171 B1 | 7/2006 | Muffoletto et al. | |
| 7,085,126 B2 | 8/2006 | Muffoletto et al. | |
| 7,092,242 B1 | 8/2006 | Gloss et al. | |
| 7,099,143 B1 | 8/2006 | Fife et al. | |
| 7,220,397 B2 | 5/2007 | Kimmel et al. | |
| 7,341,705 B2 | 3/2008 | Schnitter | |
| 7,381,396 B2 | 6/2008 | Thomas et al. | |
| 7,419,926 B2 | 9/2008 | Schnitter et al. | |
| 7,456,073 B2 | 11/2008 | Fife et al. | |
| 7,460,356 B2 | 12/2008 | Ning | |
| 7,480,130 B2 | 1/2009 | Fife et al. | |
| 7,483,260 B2 | 1/2009 | Ziarniak et al. | |
| 7,511,943 B2 | 3/2009 | Fife et al. | |
| 7,515,396 B2 | 4/2009 | Biler | |
| 7,554,792 B2 | 6/2009 | Ning | |
| 7,645,538 B1 | 1/2010 | Hallifax et al. | |
| 7,649,730 B2 | 1/2010 | Jones et al. | |
| 7,710,713 B2 | 5/2010 | Restorff et al. | |
| 7,773,367 B1 * | 8/2010 | Knowles | H01G 9/022 361/523 |
| 7,804,676 B2 | 9/2010 | Brendel et al. | |
| 7,813,107 B1 | 10/2010 | Druding et al. | |
| 7,867,293 B1 | 1/2011 | Moceri et al. | |
| 7,875,379 B2 | 1/2011 | Moceri et al. | |
| 7,968,817 B2 | 6/2011 | Freitag et al. | |
| 7,983,022 B2 | 7/2011 | O'Connor et al. | |
| 8,023,250 B2 | 9/2011 | Ning et al. | |
| 8,027,149 B2 | 9/2011 | Druding et al. | |
| 8,081,419 B2 | 12/2011 | Monroe et al. | |
| 8,086,312 B2 | 12/2011 | Nielsen et al. | |
| 8,130,487 B2 | 3/2012 | Shimizu et al. | |
| 8,259,435 B2 | 9/2012 | Millman et al. | |
| 8,405,956 B2 | 3/2013 | Dreissig et al. | |
| 8,451,586 B2 | 5/2013 | Priban | |
| 8,477,479 B2 | 7/2013 | Pease et al. | |
| 8,514,547 B2 | 8/2013 | Galvagni et al. | |
| 8,605,411 B2 | 12/2013 | Biler et al. | |
| 8,687,347 B2 | 4/2014 | Bates et al. | |
| 8,737,041 B2 | 5/2014 | Shimizu et al. | |
| 8,824,121 B2 | 9/2014 | Biler et al. | |
| 8,968,423 B2 | 3/2015 | Biler | |
| 8,971,019 B2 | 3/2015 | Biler | |
| 8,971,020 B2 | 3/2015 | Biler et al. | |
| 9,053,861 B2 | 6/2015 | Weaver et al. | |
| 9,076,592 B2 | 7/2015 | Masheder et al. | |
| 9,105,401 B2 | 8/2015 | Dreissig et al. | |
| 9,129,747 B2 | 9/2015 | Pinwill et al. | |
| 9,165,718 B2 | 10/2015 | Petrzilek | |
| 9,183,991 B2 | 11/2015 | Petrzilek et al. | |
| 9,218,913 B2 | 12/2015 | Biler | |
| 9,275,799 B2 | 3/2016 | Karnik et al. | |
| 9,384,901 B2 | 7/2016 | Weaver | |
| 2012/0106030 A1 * | 5/2012 | Millman | H01G 9/08 361/518 |
| 2013/0242467 A1 * | 9/2013 | Biler | C09D 5/4476 361/504 |
| 2016/0038751 A1 | 2/2016 | Broder et al. | |
| 2016/0141110 A1 * | 5/2016 | Djebara | H01G 9/10 607/119 |

FOREIGN PATENT DOCUMENTS

| | | |
|---|---|---|
| EP | 1 818 957 B1 | 6/2011 |
| EP | 1 936 643 B1 | 6/2012 |

* cited by examiner

WET ELECTROLYTIC CAPACITOR

BACKGROUND OF THE INVENTION

An implantable cardioverter-defibrillator ("ICD") is a medical device combining a cardioverter and a defibrillator into a single implantable unit. One type of ICD is implanted intravascularly or intracardially, having leads positioned within the heart as well as being attached to the outer surface of the heart. Such ICDs require the plurality of high energy capacitors to provide about 35 to 40 joules of energy per electrical impulse, as well as having a high voltage per electrical impulse in the range of 700 to 800 volts to properly defibrillate, for example, a patient suffering from ventricular fibrillation. Another kind of ICD is implanted subcutaneously and includes leads that are placed under the skin and without direct contact with the heart. Such ICDs are also known in the art as "subcutaneous ICDs." The electrical impulse in a subcutaneous ICD needs to pass through muscles, the lungs and bones to defibrillate the heart as the leads are placed subcutaneously and are not in contact with the heart. As such, subcutaneous ICDs must employ even higher energy and voltage levels than intracardiac ICDs. Wet electrolytic capacitors are used in most state of the art ICDs due to their ability to store high energy levels as well as their ability to maintain high voltages, and thus have a high volumetric efficiency. The most common capacitor shape used in ICDs is in the form of a half circle or "D shape." Such D-shaped capacitors are not, however, suitable for use in many types of implantable subcutaneous devices due to their low ratio between capacitance and size. While cylindrically-shaped capacitors seem to be an ideal candidate, such capacitors often experience increased DC leakage current.

As such, a need still exists for an improved wet electrolytic capacitor for use in subcutaneous ICDs.

SUMMARY OF THE INVENTION

In accordance with one embodiment of the present invention, a wet electrolytic capacitor is disclosed that comprises a casing that contains a sidewall extending to an upper end to define an opening, wherein the sidewall further defines an inner surface that surrounds an interior. At least one anode and at least one cathode are positioned within the interior of the casing, wherein the cathode contains an electrochemically-active material and further wherein an anode lead extends from the anode. A working electrolyte is in electrical contact with the anode and the electrochemically-active material. The capacitor also comprises a lid assembly that contains a lid positioned on an upper end of the casing sidewall, wherein the lid defines an orifice through which a tube extends. The tube accommodates the anode lead that extends from the anode. A dielectric layer is formed on a surface of the tube.

Other features and aspects of the present invention are described in more detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
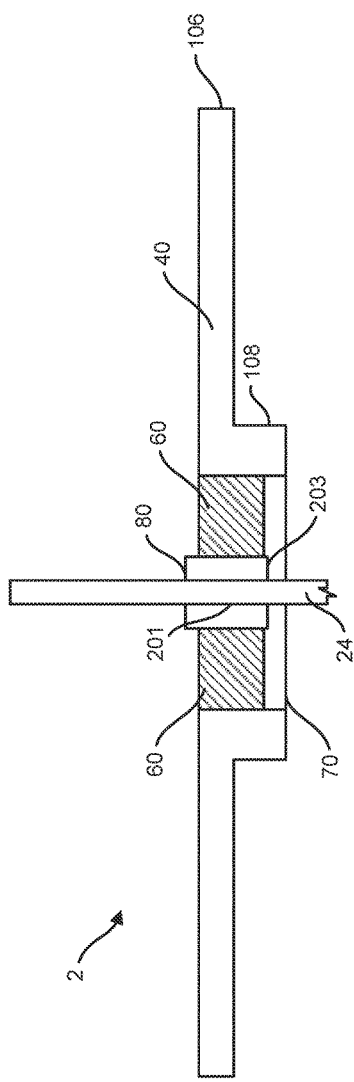
FIG. 1 is a cross-sectional view of one embodiment of a lid assembly that may be used to seal the wet electrolytic capacitor of the present invention.

Repeat use of reference characters in the present specification and drawings is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to a wet electrolytic capacitor that contains a casing having a sidewall extending to an opening. The sidewall defines an inner surface that surrounds an interior of the casing. An anode, cathode, and working electrolyte are positioned within the interior of the casing. Furthermore, a lid assembly seals the opening of the casing. The lid assembly contains a lid (e.g., tantalum) that defines an internal orifice. A tube extends through the orifice that is of a size and shape sufficient to accommodate an anode lead that extends from the anode. The tube is generally formed from a valve metal, such as tantalum, niobium, aluminum, nickel, hafnium, titanium, silver, alloys thereof (e.g., electrically conductive oxides), and so forth. Notably, a dielectric layer is formed on a surface (inner and/or exterior surfaces) of the tube. Without intending to be limited by theory, it is believed that the dielectric layer can help to prevent the tube from direct contact with the working electrolyte and thus minimize DC leakage current. To help further minimize leakage current, the thickness of the dielectric layer on the tube typically ranges from about 10 nanometers to about 1,000 nanometers, in some embodiments from about 15 nanometers to about 800 nanometers, in some embodiments from about 20 nanometers to about 600 nanometers, and some embodiments, from about 30 nanometers to about 500 nanometers.

Various embodiments of the present invention will now be described in further detail.

I. Anode

The anode(s) of the electrolytic capacitor typically include a porous body that may be formed from a valve metal composition. The valve metal composition contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal composition may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. For example, the niobium oxide may be $NbO_{0.7}$, $NbO_{1.0}$, $NbO_{1.1}$, and $NbO_2$. Examples of such valve metal oxides are described in U.S. Pat. No. 6,322,912 to Fife; U.S. Pat. No. 6,391,275 to Fife et al.; U.S. Pat. No. 6,416,730 to Fife et al.; U.S. Pat. No. 6,527,937 to Fife; U.S. Pat. No. 6,576,099 to Kimmel, et al.; U.S. Pat. No. 6,592,740 to Fife, et al.; and U.S. Pat. No. 6,639,787 to Kimmel, et al.; and U.S. Pat. No. 7,220,397 to Kimmel, et al., as well as U.S. Patent Application Publication Nos. 2005/0019581 to Schnitter; 2005/0103638 to Schnitter, et al.; 2005/0013765 to Thomas, et al.

To form an anode, a powder of the valve metal composition is generally employed. The powder may contain particles any of a variety of shapes, such as nodular, angular, flake, etc., as well as mixtures thereof. Particularly suitable powders are tantalum powders available from Cabot Corp. (e.g., C255 flake powder, TU4D flake/nodular powder, etc.) and H. C. Starck (e.g., NH175 nodular powder). The powder may be formed using techniques known to those skilled in the art. A precursor tantalum powder, for instance, may be formed by reducing a tantalum salt (e.g., potassium fluotantalate ($K_2TaF_7$), sodium fluotantalate ($Na_2TaF_7$), tantalum pentachloride ($TaCl_5$), etc.) with a reducing agent (e.g., hydrogen, sodium, potassium, magnesium, calcium, etc.). Any of a variety of milling techniques may be utilized in the present invention to achieve the desired particle characteristics. For example, the powder may be dispersed in a fluid medium (e.g., ethanol, methanol, fluorinated fluid, etc.) to form a slurry. The slurry may then be combined with a grinding media (e.g., metal balls, such as tantalum) in a mill. The number of grinding media may generally vary depending on the size of the mill, such as from about 100 to about 2000, and in some embodiments from about 600 to about 1000. The starting powder, the fluid medium, and grinding media may be combined in any proportion. For example, the ratio of the starting valve metal powder to the grinding media may be from about 1:5 to about 1:50. Likewise, the ratio of the volume of the fluid medium to the combined volume of the starting valve metal powder may be from about 0.5:1 to about 3:1, in some embodiments from about 0.5:1 to about 2:1, and in some embodiments, from about 0.5:1 to about 1:1. Some examples of mills that may be used in the present invention are described in U.S. Pat. Nos. 5,522,558; 5,232,169; 6,126,097; and 6,145,765.

Milling may occur for any predetermined amount of time needed to achieve the target specific surface area. For example, the milling time may range from about 30 minutes to about 40 hours, in some embodiments, from about 1 hour to about 20 hours, and in some embodiments, from about 5 hours to about 15 hours. Milling may be conducted at any desired temperature, including at room temperature or an elevated temperature. After milling, the fluid medium may be separated or removed from the powder, such as by air-drying, heating, filtering, evaporating, etc. For instance, the powder may optionally be subjected to one or more acid leaching steps to remove metallic impurities. Such acid leaching steps are well known in the art and may employ any of a variety of acids, such as mineral acids (e.g., hydrochloric acid, hydrobromic acid, hydrofluoric acid, phosphoric acid, sulfuric acid, nitric acid, etc.), organic acids (e.g., citric acid, tartaric acid, formic acid, oxalic acid, benzoic acid, malonic acid, succinic acid, adipic acid, phthalic acid, etc.); and so forth.

Although not required, the powder may be agglomerated using any technique known in the art. Such powders may be agglomerated in a variety of ways, such as through one or multiple heat treatment steps at a temperature of from about 700° C. to about 1400° C., in some embodiments from about 750° C. to about 1200° C., and in some embodiments, from about 800° C. to about 1100° C. Heat treatment may occur in an inert or reducing atmosphere. For example, heat treatment may occur in an atmosphere containing hydrogen or a hydrogen-releasing compound (e.g., ammonium chloride, calcium hydride, magnesium hydride, etc.) to partially sinter the powder and decrease the content of impurities (e.g., fluorine). If desired, agglomeration may also be performed in the presence of a getter material, such as magnesium. After thermal treatment, the particles may be passivated by the gradual admission of air. Other suitable agglomeration techniques are also described in U.S. Pat. No. 6,576,038 to Rao; U.S. Pat. No. 6,238,456 to Wolf, et al.; U.S. Pat. No. 5,954,856 to Pathare, et al.; U.S. Pat. No. 5,082,491 to Rerat; U.S. Pat. No. 4,555,268 to Getz; U.S. Pat. No. 4,483,819 to Albrecht, et al.; U.S. Pat. No. 4,441,927 to Getz, et al.; and U.S. Pat. No. 4,017,302 to Bates, et al.

Certain additional components may also be included in the powder. For example, the powder may be optionally mixed with a binder and/or lubricant to ensure that the particles adequately adhere to each other when pressed. Suitable binders may include, for instance, poly(vinyl butyral); poly(vinyl acetate); poly(vinyl alcohol); poly(vinyl pyrrolidone); cellulosic polymers, such as carboxymethylcellulose, methyl cellulose, ethyl cellulose, hydroxyethyl cellulose, and methylhydroxyethyl cellulose; atactic polypropylene, polyethylene; polyethylene glycol (e.g., Carbowax™ from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly(lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

The resulting powder may be compacted using any conventional powder press mold. For example, the press mold may be a single station compaction press using a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead (e.g., tantalum wire). It should be further appreciated that the anode lead may alternatively be attached (e.g., welded) to the anode body subsequent to pressing and/or sintering of the anode body.

If desired, any binder/lubricant may be removed after compression, such as by heating the formed pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al., which is incorporated herein in its entirety by reference thereto for all purposes. Regardless, the pressed anode body is sintered to form a porous, integral mass. The sintering conditions may be within the ranges noted above.

The sintered anode body may then be anodically oxidized ("anodized") so that a dielectric layer is formed over and/or within the anode. For example, a tantalum (Ta) anode body may be anodized to form a dielectric layer of tantalum pentoxide ($Ta_2O_5$). Anodization may be performed by initially applying an electrolyte to the anode body, such as by dipping the anode body into a bath that contains the electrolyte, and then applying a current. The electrolyte is generally in the form of a liquid, such as a solution (e.g., aqueous or non-aqueous), dispersion, melt, etc. A solvent is generally employed in the electrolyte, such as water (e.g., deionized water); ethers (e.g., diethyl ether and tetrahydrofuran); alcohols (e.g., methanol, ethanol, n-propanol, isopropanol, and butanol); triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. The solvent may constitute from about 50 wt. % to about 99.9 wt. %, in some embodiments from about 75 wt. % to about 99 wt. %, and in some embodiments, from about 80 wt. % to about 95 wt. % of the electrolyte. Although not necessarily required, the use of an aqueous solvent (e.g., water) is often desired to facilitate formation of an oxide. In fact, water may constitute about 1 wt. % or more, in some embodiments about 10 wt. % or more, in some embodiments about 50 wt. % or more, in some embodiments about 70 wt. % or more, and in some embodiments, about 90 wt. % to 100 wt. % of the solvent(s) used in the electrolyte.

The electrolyte is electrically conductive and may have an electrical conductivity of about 0.05 milliSiemens per centimeter ("mS/cm") or more, in some embodiments about 0.1 mS/cm or more, and in some embodiments, from about 0.2 mS/cm to about 100 mS/cm, determined at a temperature of 25° C. To enhance the electrical conductivity of the electrolyte, a compound may be employed that is capable of dissociating in the solvent to form ions. Suitable ionic compounds for this purpose may include, for instance, acids, such as hydrochloric acid, nitric acid, sulfuric acid, phosphoric acid, polyphosphoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, dodecylsulfonic acid, dodecylbenzenesulfonic acid, etc.; polymeric acids, such as poly(acrylic) or poly(methacrylic) acid and copolymers thereof (e.g., maleic-acrylic, sulfonic-acrylic, and styrene-acrylic copolymers), carageenic acid, carboxymethyl cellulose, alginic acid, etc.; and so forth. The concentration of ionic compounds is selected to achieve the desired electrical conductivity. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the electrolyte. If desired, blends of ionic compounds may also be employed in the electrolyte.

A current is passed through the electrolyte to form the dielectric layer. The value of voltage manages the charge (current multiplied by time) and thereby the thickness of the dielectric layer. For example, the power supply may be initially set up at a galvanostatic mode until the required voltage is reached. Thereafter, the power supply may be switched to a potentiostatic mode in which the voltage is held constant to ensure that the desired dielectric thickness is formed on the anode body. Of course, other known methods may also be employed, such as pulse methods. Regardless, to help achieve the desired thickness for the dielectric layer, the forming voltage used during anodization, which is typically equal to the peak voltage, is typically high, such as about 150 volts or more, in some embodiments from about 200 volts to about 350 volts, and in some embodiments, from about 220 to about 320 volts. The voltage level may vary (e.g., increasing) or remain constant within this range. The temperature of the anodizing solution may range from about 10° C. to about 200° C., in some embodiments from about 20° C. to about 150° C., and in some embodiments, from about 30° C. to about 100° C.

The size of the resulting anode may depend in part on the desired size of the capacitor. In certain embodiments, the length of the anode body may range from about 10 to about 200 millimeters, in some embodiments from about 15 to about 150 millimeters, and in some embodiments, from about 20 to about 120 millimeters. The width (or diameter) of the anode may also range from about 0.5 to about 20 millimeters, in some embodiments from about 1 to about 20 millimeters, and in some embodiments, from about 2 to about 10 millimeters. The length of the capacitor may likewise range from about 20 to about 300 millimeters, in some embodiments from about 40 to about 200 millimeters, and in some embodiments, from about 50 to about 150 millimeters. The width (or diameter) of the capacitor may also range from about 1 to about 30 millimeters, in some embodiments from about 2 to about 20 millimeters, and in some embodiments, from about 5 to about 15 millimeters.

II. Cathode

The cathode(s) of the capacitor generally contains an electrochemically-active material, which may be coated onto a metal substrate. The metal substrate may form the all or a portion of casing for the capacitor, or it may simply be a separate material (e.g., foil, sheet, screen, mesh, etc.) that is disposed in proximity to an anode. Regardless, the metal used to form the casing and/or metal substrate may include, for instance, tantalum, niobium, aluminum, nickel, hafnium, titanium, copper, silver, steel (e.g., stainless), alloys thereof, composites thereof (e.g., metal coated with electrically conductive oxide), and so forth. Tantalum is particularly suitable for use in the present invention. If desired, a surface of the substrate may be roughened to increase its surface area and increase the degree to which a material may be able to adhere thereto. In one embodiment, for example, a surface of the substrate is chemically etched, such as by applying a solution of a corrosive substance (e.g., hydrochloric acid) to the surface. Mechanical roughening may also be employed. For instance, a surface of the substrate may be abrasive blasted by propelling a stream of abrasive media (e.g., sand) against at least a portion of a surface thereof.

Once formed, an electrochemically-active material is applied to the metal substrate to increase the effective surface area (e.g., carbonaceous particles) and/or provide pseudo-capacitance (e.g., conductive polymers, ruthenium oxide, etc.) to produce a high capacitance cathode with which the electrolyte electrochemically communicates with the substrate. Such a high capacity cathode material allows for the formation of capacitors with maximized capacitance for a given size and/or capacitors with a reduced size for a given capacitance. The nature of the electrochemically-active material may vary. For example, a particulate material may be employed that includes conductive particles, such as those formed from tantalum, ruthenium, iridium, nickel, rhodium, rhenium, cobalt, tungsten, manganese, tantalum, niobium, molybdenum, lead, titanium, platinum, palladium, and osmium, as well as combinations of these metals. Non-insulating oxide conductive particles may also be employed. Suitable oxides may include a metal selected from the group consisting of ruthenium, iridium, nickel, rhodium, rhenium, cobalt, tungsten, manganese, tantalum, niobium, molybdenum, lead, titanium, platinum, palladium, and osmium, as well as combinations of these metals. Particularly suitable metal oxides include ruthenium dioxide, niobium oxide, niobium dioxide, iridium oxide, and manganese dioxide. Carbonaceous particles may also be employed that have the desired level of conductivity, such as activated carbon, carbon black, graphite, etc. Some suitable forms of activated carbon and techniques for formation thereof are described in U.S. Pat. No. 5,726,118 to Ivey, et al. and U.S. Pat. No. 5,858,911 to Wellen, et al.

If desired, the particles may be sintered together and/or to the substrate so that they form a more integral and robust coating. For example, tantalum particles may be employed that form a "sleeve" over the metal substrate. Sintering may be conducted at a wide variety of temperatures, such as from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 10 minutes to about 50 minutes. This may occur in one or more steps. If desired, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

A conductive polymer coating may also be employed as the electrochemically-active material. The conductive polymer coating may be formed from one or more layers. The material employed in such layer(s) may vary. In one embodiment, for example, the material includes conductive polymer(s) that are typically π-conjugated and have electrical conductivity after oxidation or reduction. Examples of such π-conjugated conductive polymers include, for instance, polyheterocycles (e.g., polypyrroles, polythiophenes, polyanilines, etc.), polyacetylenes, poly-p-phenylenes, polyphenolates, and so forth. Substituted polythiophenes are particularly suitable for use as conductive polymer in that they have particularly good mechanical robustness and electrical performance. In one particular embodiment, the substituted polythiophene has the following general structure:

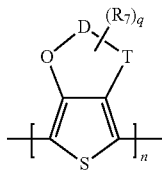

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments from 4 to 2,000, and in some embodiments, from 5 to 1,000. Example of substituents for the radicals "D" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

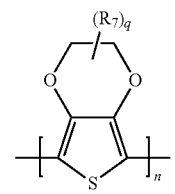

Methods for forming conductive polymers, such as described above, are well known in the art. For instance, U.S. Pat. No. 6,987,663 to Merker, et al. describes various techniques for forming substituted polythiophenes from a monomeric precursor. The monomeric precursor may, for instance, have the following structure:

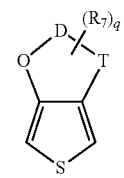

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

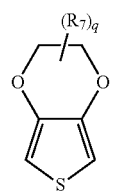

wherein, $R_7$ and q are as defined above.

In one particular embodiment, "q" is 0. One commercially suitable example of 3,4-ethylenedioxthiophene is available from Heraeus Clevios under the designation Clevios™. In yet another particular embodiment, "q" is 1. For example, an alkyl-substituted poly(3,4-dioxyethylenethiophene) may be employed. One example of such a polymer is one in which $R_7$ in the formula above is $(CH_2)_y$—$OR_2$, wherein y is from 1 to 10, in some embodiments from 1 to 5, in some embodiments, from 1 to 3, and in some embodiments, from 1 to 2 (e.g., 2); and $R_2$ is hydrogen or an alkyl group. Particular examples of such polymers include hydroxyethylated poly(3,4-ethylenedioxythiophene) (y is 2 and $R_2$ is H) and hydroxymethylated poly(3,4-ethylenedioxthiophene) (y is 1 and $R_2$ is H).

The thiophene monomers may be chemically polymerized in the presence of an oxidative catalyst. The oxidative catalyst typically includes a transition metal cation, such as iron(III), copper(II), chromium(VI), cerium(IV), manganese (IV), manganese(VII), ruthenium(III) cations, etc. A dopant may also be employed to provide excess charge to the conductive polymer and stabilize the conductivity of the polymer. The dopant typically includes an inorganic or organic anion, such as an ion of a sulfonic acid. In certain embodiments, the oxidative catalyst employed in the precursor solution has both a catalytic and doping functionality in that it includes a cation (e.g., transition metal) and anion (e.g., sulfonic acid). For example, the oxidative catalyst may be a transition metal salt that includes iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of iron (III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable. One commercially suitable example of iron(III)-p-toluene sulfonate is available from Heraeus Clevios under the designation Clevios™ C.

Various methods may be utilized to form a conductive polymer layer. In one embodiment, the oxidative catalyst and monomer are applied, either sequentially or together, such that the polymerization reaction occurs in situ on the substrate. Suitable application techniques may include screen-printing, dipping, electrophoretic coating, and spraying, may be used to form a conductive polymer coating. As an example, the monomer may initially be mixed with the oxidative catalyst to form a precursor solution. Once the mixture is formed, it may be applied to the substrate and then allowed to polymerize so that the conductive coating is formed on the surface. Alternatively, the oxidative catalyst and monomer may be applied sequentially. In one embodiment, for example, the oxidative catalyst is dissolved in an organic solvent (e.g., butanol) and then applied as a dipping solution. The substrate may then be dried to remove the solvent therefrom. Thereafter, the substrate may be dipped into a solution containing the monomer. Polymerization is typically performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Pat. No. 7,515,396 to Biler. Still other methods for applying such conductive coating(s) may be described in U.S. Pat. No. 5,457,862 to Sakata, et al., U.S. Pat. No. 5,473,503 to Sakata, et al., U.S. Pat. No. 5,729,428 to Sakata, et al., and U.S. Pat. No. 5,812,367 to Kudoh, et al.

The total target thickness of the electrochemically-active coating may generally vary depending on the desired properties of the capacitor. Typically, the coating has a thickness of from about 0.2 micrometers ("μm") to about 50 μm, in some embodiments from about 0.5 μm to about 20 μm, and in some embodiments, from about 1 μm to about 5 μm. Regardless, the resulting cathode, including the substrate and electrochemically-active material may have a relatively small thickness. For example, the cathode may have a thickness ranging from about 10 micrometers to about 2000 micrometers, in some embodiments from about 20 micrometers to about 1500 micrometers, and in some embodiments, from about 30 micrometers to about 1000 micrometers.

III. Working Electrolyte

The working electrolyte may be impregnated within the anode, or it may be added to the capacitor at a later stage of production. The electrolyte generally uniformly wets the dielectric on the anode. Various suitable electrolytes are described in U.S. Pat. Nos. 5,369,547 and 6,594,140 to Evans, et al. Typically, the electrolyte is ionically conductive in that has an electrical conductivity of from about 0.005 to about 1 Siemens per centimeter ("S/cm"), in some embodiments from about 0.01 to about 0.1 S/cm, and in some embodiments, from about 0.02 to about 0.05 S/cm, determined at a temperature of about 23° C. using any known electric conductivity meter (e.g., Oakton Con Series 11). The electrolyte is generally in the form of a fluid, such as a liquid, such as a solution (e.g., aqueous or non-aqueous), colloidal suspension, gel, etc. For example, the electrolyte may be an aqueous solution of an acid (e.g., sulfuric acid, phosphoric acid, or nitric acid), base (e.g., potassium hydroxide), or salt (e.g., ammonium salt, such as a nitrate), as well any other suitable electrolyte known in the art, such as a salt dissolved in an organic solvent (e.g., ammonium salt dissolved in a glycol-based solution). Various other electrolytes are described in U.S. Pat. Nos. 5,369,547 and 6,594,140 to Evans, et al.

The desired ionic conductivity may be achieved by selecting ionic compound(s) (e.g., acids, bases, salts, and so forth) within certain concentration ranges. In one particular embodiment, salts of weak organic acids may be effective in achieving the desired conductivity of the electrolyte. The cation of the salt may include monatomic cations, such as alkali metals (e.g., $Li^+$, $Na^+$, $K^+$, $Rb^+$, or $Cs^+$), alkaline earth metals (e.g., $Be^{2+}$, $Mg^{2+}$, $Ca^{2+}$, $Sr^{2+}$ or $Ba^{2+}$), transition metals (e.g., $Ag^+$, $Fe^{2+}$, $Fe^{3+}$, etc.), as well as polyatomic cations, such as $NH_4^+$. The monovalent ammonium ($NH_4^+$), sodium ($K^+$), and lithium ($Li^+$) are particularly suitable cations for use in the present invention. The organic acid used to form the anion of the salt may be "weak" in the sense that it typically has a first acid dissociation constant ($pK_{a1}$) of about 0 to about 11, in some embodiments about 1 to about 10, and in some embodiments, from about 2 to about 10, determined at about 23° C. Any suitable weak organic acids may be used in the present invention, such as carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid, etc.), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; blends thereof, and so forth. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40), etc.

While the actual amounts may vary depending on the particular salt employed, its solubility in the solvent(s) used in the electrolyte, and the presence of other components, such weak organic acid salts are typically present in the electrolyte in an amount of from about 0.1 to about 25 wt. %, in some embodiments from about 0.2 to about 20 wt. %, in some embodiments from about 0.3 to about 15 wt. %, and in some embodiments, from about 0.5 to about 5 wt. %.

The electrolyte is typically aqueous in that it contains an aqueous solvent, such as water (e.g., deionized water). For example, water (e.g., deionized water) may constitute from about 20 wt. % to about 95 wt. %, in some embodiments from about 30 wt. % to about 90 wt. %, and in some embodiments, from about 40 wt. % to about 85 wt. % of the electrolyte. A secondary solvent may also be employed to form a solvent mixture. Suitable secondary solvents may include, for instance, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane); and so forth. Such solvent mixtures typically contain water in an amount from about 40 wt. % to about 80 wt. %, in some embodiments from about 50 wt. % to about 75 wt. %, and in some embodiments, from about 55 wt. % to about 70 wt. % and secondary solvent(s) in an amount from about 20 wt. % to about 60 wt. %, in some embodiments from about 25 wt. % to about 50 wt. %, and in some embodiments, from about 30 wt. % to about 45 wt. %. The secondary solvent(s) may, for example, constitute from about 5 wt. % to about 45 wt. %, in some embodiments from about 10 wt. % to about 40 wt. %, and in some embodiments, from about 15 wt. % to about 35 wt. % of the electrolyte.

If desired, the electrolyte may be relatively neutral and have a pH of from about 4.5 to about 8.0, in some embodiments from about 5.0 to about 7.5, and in some embodiments, from about 5.5 to about 7.0. One or more pH adjusters (e.g., acids, bases, etc.) may be employed to help achieve the desired pH. In one embodiment, an acid is employed to lower the pH to the desired range. Suitable acids include, for instance, organic acids such as described above; inorganic acids, such as hydrochloric acid, nitric acid, sulfuric acid, phosphoric acid, polyphosphoric acid, boric acid, boronic acid, etc.; and mixtures thereof. Although the total concentration of pH adjusters may vary, they are typically present in an amount of from about 0.01 wt. % to about 10 wt. %, in some embodiments from about 0.05 wt. % to about 5 wt. %, and in some embodiments, from about 0.1 wt. % to about 2 wt. % of the electrolyte.

The electrolyte may also contain other components that help improve the electrical performance of the capacitor. For instance, a depolarizer may be employed in the electrolyte to help inhibit the evolution of hydrogen gas at the cathode of the electrolytic capacitor, which could otherwise cause the capacitor to bulge and eventually fail. When employed, the depolarizer normally constitutes from about 1 to about 500 parts per million ("ppm"), in some embodiments from about 10 to about 200 ppm, and in some embodiments, from about 20 to about 150 ppm of the electrolyte. Suitable depolarizers may include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroacetophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid, and so forth. Particularly suitable nitroaromatic depolarizers for use in the present invention are nitrobenzoic acids, anhydrides or salts thereof, substituted with one or more alkyl groups (e.g., methyl, ethyl, propyl, butyl, etc.). Specific examples of such alkyl-substituted nitrobenzoic compounds include, for instance, 2-methyl-3-nitrobenzoic acid; 2-methyl-6-nitrobenzoic acid; 3-methyl-2-nitrobenzoic acid; 3-methyl-4-nitrobenzoic acid; 3-methyl-6-nitrobenzoic acid; 4-methyl-3-nitrobenzoic acid; anhydrides or salts thereof; and so forth.

IV. Capacitor Construction

As indicated above, the wet electrolytic capacitor of the present invention contains a casing within which the working electrolyte, at least one cathode, and at least anode are positioned. As indicated above, a lid assembly seals the opening of the casing. The lid assembly contains a lid (e.g., tantalum) that defines an internal orifice. The lid is typically formed from a metal, such as tantalum, niobium, aluminum, nickel, hafnium, titanium, copper, silver, steel (e.g., stainless), alloys thereof (e.g., electrically conductive oxides), composites thereof (e.g., metal coated with electrically conductive oxide), and so forth.

A tube extends through the orifice that is hollow and of a size and shape sufficient to accommodate an anode lead that extends from an anode. The tube is generally formed from a valve metal, such as tantalum, niobium, aluminum, nickel, hafnium, titanium, silver, alloys thereof (e.g., electrically conductive oxides), and so forth. Notably, a dielectric layer is formed on a surface (inner and/or exterior surfaces) of the tube. The dielectric layer may be formed by subjecting the tube to a voltage to initiate anodic formation ("anodization") of an oxide film (dielectric layer). For example, a tantalum (Ta) tube may be anodized to form a dielectric layer of tantalum pentoxide ($Ta_2O_5$). Anodization may be performed by initially applying an electrolyte to the tube, such as by dipping the tube into a bath that contains the electrolyte, and then applying a current. The electrolyte is generally in the form of a fluid, such as described above. To help achieve the desired thickness for the dielectric layer as noted above, the forming voltage is typically, such as about 5 volts or more, in some embodiments from about 5 volts to about 200 volts, 200 volts to about 400 volts, and in some embodiments, from about 250 to about 350 volts. The voltage level may vary (e.g., increasing) or remain constant within this range.

Referring to FIG. 1, for example, one embodiment of a lid assembly 2 that may be employed in the present invention is shown in more detail. As shown, the lid assembly 2 contains a lid 40 having an upper planar surface spaced from a lower planar surface. The lid 40 defines an internal orifice (not shown), which may be cylindrical and of a generally constant inside diameter. In the illustrated embodiment, the orifice is defined by a cylindrical sidewall spaced inwardly from an inner diameter portion 108 of the lid 40. The sidewall may alternatively be formed integral with the from a separate ferrule portion connected to the lid 40. An insulative material (e.g., glass) may be provided within the orifice to form a hermetic seal 60 (e.g., glass-to-metal seal) between a tube 80 and the sidewall of the orifice. Although not expressly shown, a dielectric layer may be formed on an inner surface 201 and/or a lower surface 203 of the tube 80 as indicated above.

The particular manner in which the anode(s), cathode(s), and working electrolyte are provided within the casing may vary as desired. Any number of anodes and cathodes may generally be employed. In one embodiment, for instance, a single anode may be employed. In such an embodiment, the electrochemically-active material of the cathode may be disposed on the inner surface of the casing or on a separate metal substrate (e.g., foil, sheet, screen, mesh, etc.) that is disposed in proximity to the inner surface of the casing. In other embodiments, however, the capacitor may contain multiple anodes, such as 2 or more, in some embodiments 3 or more, and in some embodiments, from 3 to 6 anodes. In one particular embodiment, multiple anodes are employed. For example, at least one central anode may be positioned within the interior of the casing and between first and second outer anodes. In certain embodiments, the central anode may define first and second opposing planar sidewalls, and the first and second outer anodes each define a radiused sidewall having a degree of curvature that, in certain embodiments, can correspond to the degree of curvature of the cylindrical sidewall of the casing. The first and second outer anodes also each define a planar sidewall that opposes the respective radiused sidewalls and faces a planar sidewall of the central anode. That is, one planar sidewall of the central anode faces the planar sidewall of the first outer anode and the opposing planar sidewall of the central anode faces the planar sidewall of the second outer anode. Without intending to be limited by theory, it is believed that such a geometric configuration for the anode can help improve the electrical properties of the resulting capacitor, and also to aid in its manufacture. It should be understood, however, that others shapes may be employed for the outer sidewalls. In certain embodiments, for example, the outer sidewalls may have rounded corners. Likewise, the outer sidewalls may be radiused. In such embodiments, the planar inner sidewalls may extend in a direction that is generally perpendicular to a line that is tangent to the radiused outer sidewalls. The number of central anodes may vary as is known in the art. For instance, the capacitor may contain 1 or more central anodes, in some embodiments from 1 to 4 central anodes, and in some embodiments, from 1 to 3 central anodes. When multiple central anodes are employed, they may have the same or different shape. For example, one central anode may possess planar sidewalls, while another may contain only radiused sidewalls.

Figure 2:
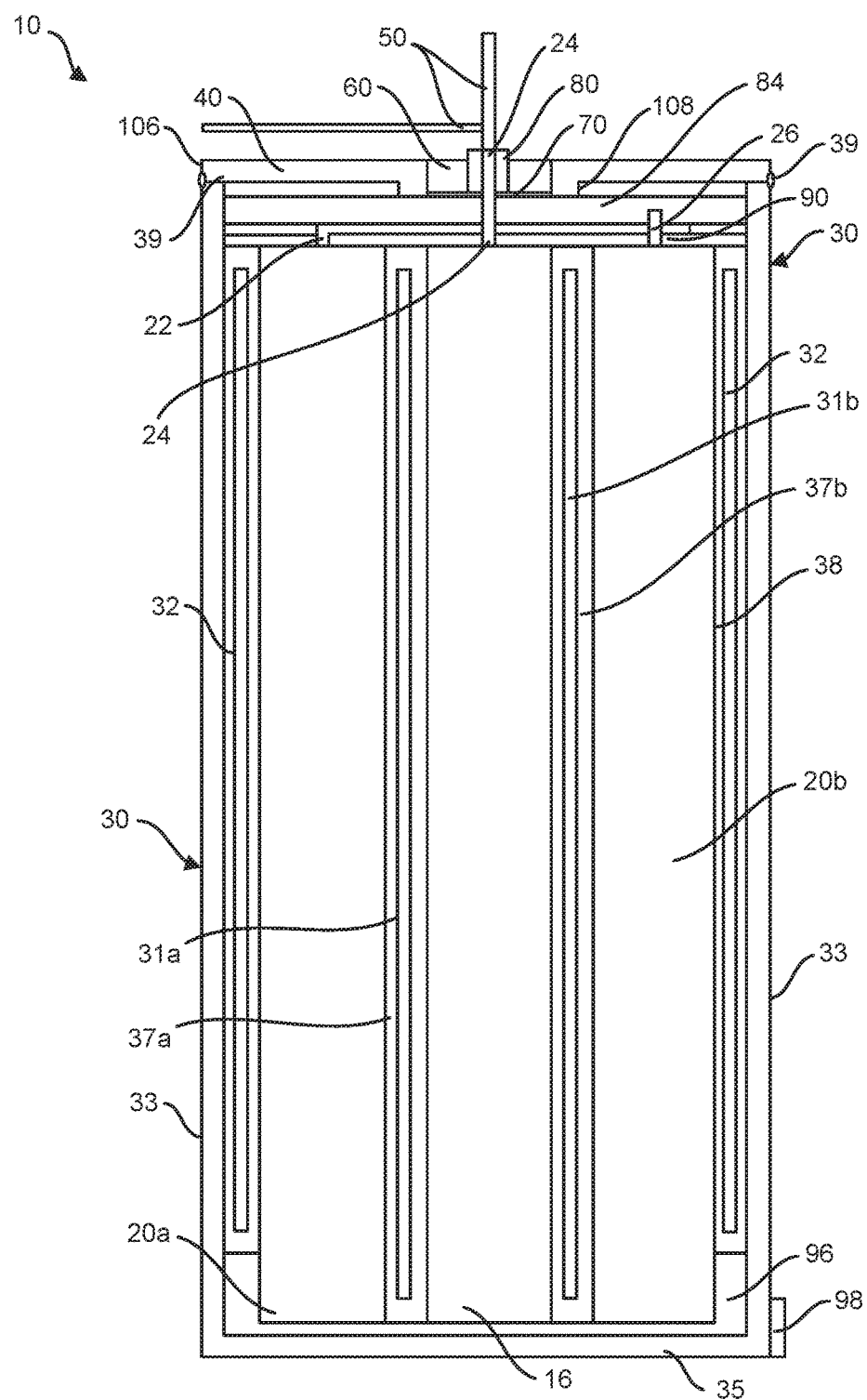
FIG. 2 is a cross-sectional view of one embodiment of the wet electrolytic capacitor of the present invention.
Figure 3:
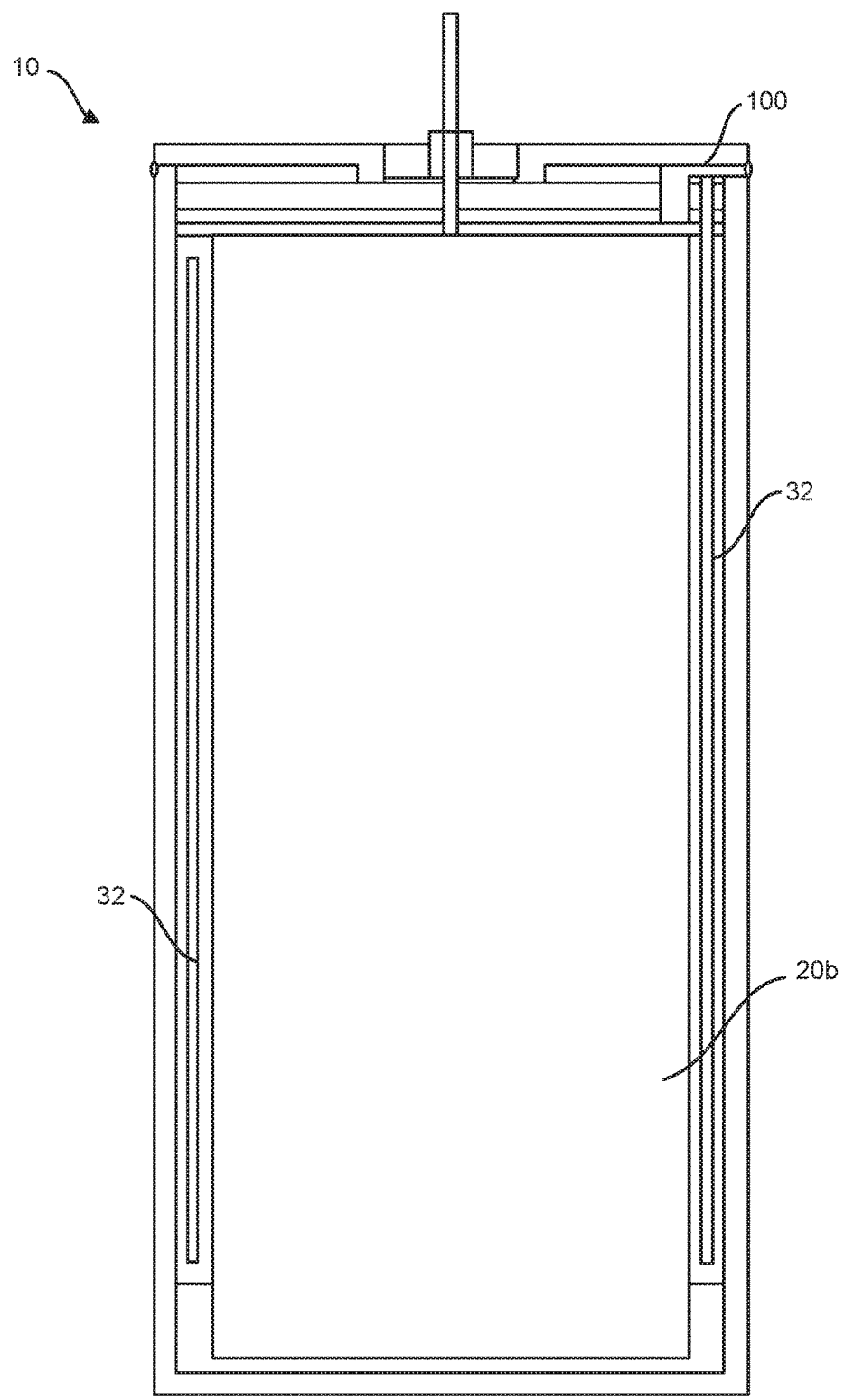
FIG. 3 is a side view of the wet electrolytic capacitor of FIG. 1.
Figure 4:
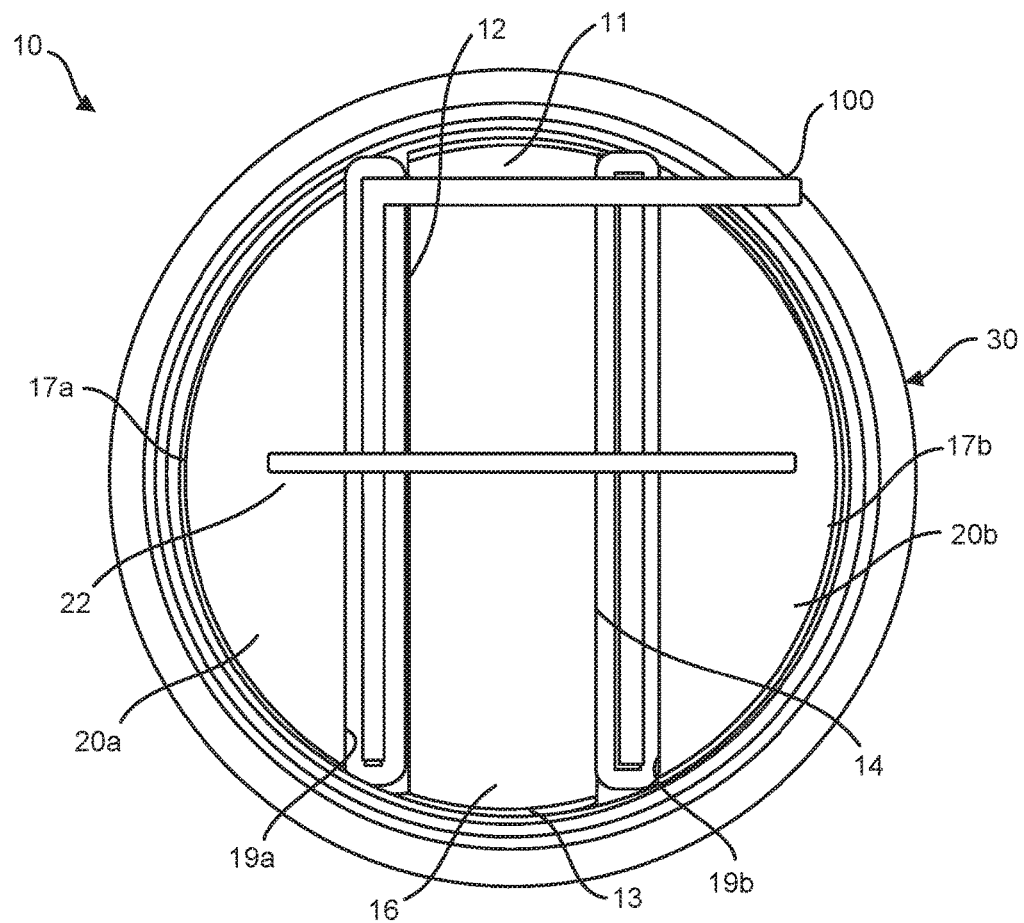
FIG. 4 is a top view of the wet electrolytic capacitor of FIG. 1, shown without a lid and sealing assembly.

Referring to FIGS. 2-4, for example, one example of a capacitor 10 containing a central anode 16 positioned between first and second outer anodes 20a and 20b is shown in more detail. As depicted, the capacitor 10 contains a casing 30 that has a sidewall 33 that extends from a bottom end 35 to an upper end 39. In the illustrated embodiment, the sidewall 33 is shown as having a cylindrical shape, but it should be understood that other shapes may also be used. Regardless, the casing 30 defines an interior within which the central anode 16 and first and second outer anodes 20a and 20b, respectively, are positioned. The central anode 16 has first and second outer sidewalls 11 and 13 that intersect first and second planar inner sidewalls 12 and 14 (FIG. 4). Likewise, as shown in FIG. 4, the first outer anode 20a has a radiused sidewall 17a and an opposing planar sidewall 19a, while the second outer anode 20b has a radiused sidewall 17b and an opposing planar sidewall 19b. In the illustrated embodiment, the planar sidewall 12 of the central anode 16 faces the planar sidewall 17a of the first outer anode 20a and the planar sidewall 14 of the central anode 16 faces the planar sidewall 17b of the second outer anode 20b.

The manner in which the anodes are connected can vary. In certain embodiments, for example, anode leads may extend in a longitudinal direction from each respective anode, which are then connected together by welding or other suitable techniques. In one embodiment, for instance, the anode leads may be connected to a common metal bridge (e.g., bar, hoop, etc.). In yet other embodiments, the leads may be directly connected together. In the illustrated embodiment, for example, an anode lead 24 extends from the central anode 16, an anode lead 22 extends from the first outer anode 20a, and an anode lead 26 extends from the second outer anode 20b. The anode lead 22 has a length that is greater than the other leads 24 and 26. In this manner, the anode lead 22 can be folded over so that it contacts both the anode lead 24 and the anode lead 26. Connection can thus be made at the point of contact. It should of course be understood that the other leads may also be folded in one or more directions to provide the desired point of contact.

As indicated above, at least one cathode is also positioned within the casing. Referring again to FIGS. 2-4, for instance, a first cathode 32 can be disposed in proximity to the inner surface of the casing sidewall 33 so that it extends around the perimeter thereof. Additional cathodes may also be disposed between the anodes. For example, a second cathode 31a may be disposed between the first outer anode 20a and the central anode 16, while a third cathode 31b may be disposed between the second outer anode 20b and the central anode 16. Although not shown, the cathodes 32, 31a, and 31b may be formed from an electrochemically-active material that is disposed on a metal substrate (e.g., foil).

If desired, a separator may also be positioned adjacent to the anodes to prevent direct contact between the anode and cathode, yet permit ionic current flow of the electrolyte to the electrodes. Examples of suitable materials for this purpose include, for instance, porous polymer materials (e.g., polypropylene, polyethylene, polycarbonate, etc.), porous inorganic materials (e.g., fiberglass mats, porous glass paper, etc.), ion exchange resin materials, etc. Particular examples include ionic perfluoronated sulfonic acid polymer membranes (e.g., Nafion™ from the E.I. DuPont de Nemeours & Co.), sulphonated fluorocarbon polymer membranes, polybenzimidazole (PBI) membranes, and polyether ether ketone (PEEK) membranes. Although preventing direct contact between the anode and cathode, the separator permits ionic current flow of the electrolyte to the electrodes. The location and configuration of a separator may vary as desired. In the embodiment illustrated in FIGS. 2-4, for instance, a first separator 38 may be wrapped around the first cathode 32 to prevent direct contact with the outer anodes 20a and 20b. Likewise, a second separator 37a may be wrapped around the second cathode 31a to prevent direct contact with the first outer anode 20a and the central anode 16, while a third separator 37b may be wrapped around the third cathode 31b to prevent direct contact with the second outer anode 20b and the central anode 16.

Referring again to FIGS. 1-4, for example, the lid assembly 2 may be used to seal the capacitor 10. As shown, the lid assembly 2 contains a lid 40 having an upper planar surface spaced from a lower planar surface. The lower planar surface of the lid 40 is positioned on and optionally welded to the upper end 39 of the casing sidewall 33 so that an outer diameter 106 of the lid 40 is coplanar to the outer diameter of the casing sidewall 33. If desired, a portion 100 of the cathode 32, cathode 31a, and/or 31b may also be positioned between the lid 40 and the upper end 39 of the casing sidewall 33. The outer diameter 106 of the lid 40 also forms a step that leads to an inner diameter portion 108. As noted above, the lid assembly 2 also contains the tube 80, which can accommodate an anode lead 24 that extends from the central anode 16.

The lid assembly may also optionally include a liquid seal 70 that is formed from a generally insulative sealant material. For example, the sealant material typically has an electrical resistance of about $1 \times 10^2$ ohms-m or more, in some embodiments about $1 \times 10^5$ ohms-m or more, and in some embodiments, from about $1 \times 10^{15}$ to about $1 \times 10^{25}$ ohms-m, determined at a temperature of 20° C. The liquid seal 70 may cover a portion of a surface of the tube 80, and preferably, the entire surface. Examples of suitable sealant materials for use in the liquid seal 70 may include, for instance, silicone polymers, flouropolymers, etc. In addition to the liquid seal discussed above, the capacitor of the present invention may also contain one or more secondary liquid seals. Referring to FIG. 2, for example, a gasket 90 is shown that is located adjacent to an upper surface of the central anode 16 and the outer anodes 20a and 20b. The gasket 90 generally has a cylindrical shape and contains a bore coaxially located therein through which the anode lead 24 can extend. The gasket 90 may be formed from any of a variety of insulative materials, such as described above (e.g., PTFE). An elastomeric washer 84 may also be employed as an additional liquid seal. If desired, the washer 84 may be positioned between the liquid seal 70 and the gasket 90 and thereby and help inhibit leakage of the electrolyte therethrough. The elastomeric washer 84 may be formed from an elastomer that is resistant to corrosion by the electrolyte and has sufficient dielectric strength to withstand the maximum voltage generated by the capacitor. Examples of elastomers that may be employed include butyl rubber, chlorobutyl rubber, ethylene propylene rubber (EPR), ethylene propylene diene rubber (EPDM), fluoroelastomers (e.g., VITON™), polytetrafluoroethylene, polychloroprene rubber, butadiene rubber, nitrile rubber, isoprene rubber, silicone rubber and styrene butadiene rubber.

To attach the lid assembly, it is generally positioned such that the liquid seal 70 is adjacent to the elastomeric washer 90. Once in the desired position, pressure may be applied to the assembly 50 to compress the elastomeric washer 90 and create a secondary liquid seal. Thereafter, the lid 40 is welded to the sidewall 33 of the casing 30. The anode lead 24 extends through the tube 80 and is sealed thereto at the outer end by a weld joint (not shown). An external positive lead 50, preferably of nickel, may likewise be welded to the tube 80. Similarly, an external negative lead 98 may be welded to the casing 30.

Regardless of the particular configuration, the resulting capacitor of the present invention may exhibit excellent electrical properties. For example, the capacitor may exhibit a high volumetric efficiency, such as from about 20,000 $\mu F^*V/cm^3$ to about 100,000 $\mu F^*V/cm^3$, in some embodiments from about 30,000 $\mu F^*V/cm^3$ to about 200,000 $\mu F^*V/cm^3$, and in some embodiments, from about 40,000 $\mu F^*V/cm^3$ to about 150,000 $\mu F^*V/cm^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 $\mu F$, which results in a product of 91,000 $\mu F^*V$. If the part occupies a volume of about 0.8 $cm^3$, this results in a volumetric efficiency of about 113,750 $\mu F^*V/cm^3$.

The capacitor may also exhibit a high energy density that enables it suitable for use in high pulse applications. Energy density is generally determined according to the equation $E=\frac{1}{2}*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter ($J/cm^3$) or more, in some embodiments about 3.0 $J/cm^3$, in some embodiments from about 3.5 $J/cm^3$ to about 10.0 $J/cm^3$, and in some embodiments, from about 4.0 to about 8.0 $J/cm^3$. The capacitor may also exhibit a relatively high "breakdown voltage" (voltage at which the capacitor fails), such as about 180 volts or more, in some embodiments about 200 volts or more, in some embodiments about 250 volts or more, and in some embodiments about 300 volts or more. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 2 $nA/\mu F^*V$, in some embodiments less than about 1 $nA/\mu^*V$, and in some embodiments, less than about 0.5 $nA/\mu F^*V$, where nA is nanoamps and $\mu F^*V$ is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such normalized leakage current values may even be maintained for a substantial amount of time at high temperatures, such as described above.

Through a unique and controlled combination of features relating to the capacitor configuration and sealing assembly, the present inventor has discovered that good electrical properties (e.g., ESR stability) can be maintained during the capacitor life operation (e.g., 18 years or more at about 37° C.). For instance, the capacitor of the present invention may exhibit an ESR of about 3,000 milliohms or less, in some embodiments less than about 2,000 milliohms, in some embodiments from about 1 to about 1,000 milliohms, and in some embodiments, from about 50 to about 800 milliohms, measured with a 2-volt bias and 1-volt signal at a frequency of 120 Hz.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A wet electrolytic capacitor comprising:
    a casing that contains a sidewall extending to an upper end to define an opening, wherein the sidewall further defines an inner surface that surrounds an interior;
    at least one anode and at least one cathode positioned within the interior of the casing, wherein the cathode contains an electrochemically-active material and further wherein an anode lead extends from the anode;
    a working electrolyte that is in electrical contact with the anode and the electrochemically-active material;
    a lid assembly that contains a lid positioned on an upper end of the casing sidewall, wherein the lid defines an orifice through which a tube extends, wherein the tube accommodates the anode lead that extends from the anode, and further wherein a dielectric layer is formed on a surface of the tube.

2. The wet electrolytic capacitor of claim 1, wherein the dielectric layer is formed on an inner surface of the tube, a lower surface of the tube, or both.

3. The wet electrolytic capacitor of claim 1, wherein the dielectric layer has a thickness of from about 30 to about 500 nanometers.

4. The wet electrolytic capacitor of claim 1, wherein the anode contains a sintered porous body on which a dielectric layer is formed.

5. The wet electrolytic capacitor of claim 1, wherein the tube is formed from a valve metal.

6. The wet electrolytic capacitor of claim 5, wherein the valve metal is tantalum.

7. The wet electrolytic capacitor of claim 1, wherein the anode includes tantalum.

8. The wet electrolytic capacitor of claim 1, wherein the sidewall has a cylindrical shape.

9. The wet electrolytic capacitor of claim 1, wherein the electrochemically-active material includes a conductive polymer.

10. The wet electrolytic capacitor of claim 1, wherein the electrochemically-active material includes sintered tantalum particles.

11. The wet electrolytic capacitor of claim 1, wherein the electrochemically-active material is coated onto a metal substrate.

12. The wet electrolytic capacitor of claim 11, wherein the metal substrate is formed from tantalum.

13. The wet electrolytic capacitor of claim 1, wherein the cathode is disposed in proximity to an inner surface of the casing sidewall.

14. The wet electrolytic capacitor of claim 1, wherein the electrolyte is aqueous and has a pH of from about 4.5 to about 8.0.

15. The wet electrolytic capacitor of claim 1, wherein the capacitor contains multiple anodes positioned within the interior of the casing.

16. The wet electrolytic capacitor of claim 15, wherein the capacitor contains first and second outer anodes positioned within the interior of the casing and a central anode positioned within the interior of the casing between the first and second outer anodes.

17. The wet electrolytic capacitor of claim 16, wherein an anode lead extends from the central anode, the first outer anode, and the second outer anode, respectively.

18. The wet electrolytic capacitor of claim 17, wherein the anode lead extending from the first outer anode is folded to contact the anode lead extending from the central anode and the anode lead extending from the second outer anode.

19. The wet electrolytic capacitor of claim 16, wherein a first cathode is disposed in proximity to an inner surface of the casing sidewall.

20. The wet electrolytic capacitor of claim 19, wherein a second cathode is disposed between the first outer anode and the central anode and a third cathode is disposed between the second outer anode and the central anode.

21. The wet electrolytic capacitor of claim 1, further comprising an external positive lead that is sealed at an end of the tube and an external negative lead that is sealed to the casing.

22. The wet electrolytic capacitor of claim 1, wherein an insulative material is provided within the orifice to form a hermetic seal between the tube and a sidewall of the orifice.

23. The wet electrolytic capacitor of claim 1, further comprising a liquid seal that covers at least a portion of the tube.

24. The wet electrolytic capacitor of claim 1, further comprising a gasket that is positioned adjacent to an upper surface of the anode.

25. The wet electrolytic capacitor of claim 24, further comprising an elastomeric washer that is positioned adjacent to the gasket.

* * * * *